(12) United States Patent
Haecker et al.

(10) Patent No.: US 9,616,471 B2
(45) Date of Patent: Apr. 11, 2017

(54) RINSING LINE, MEDICAL TECHNICAL FUNCTIONAL DEVICE, MEDICAL TECHNICAL TREATMENT APPARATUS AND METHOD

(75) Inventors: Juergen Haecker, Neu-Anspach (DE); Soeren Gronau, Bad Nauheim (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 349 days.

(21) Appl. No.: 13/811,468

(22) PCT Filed: Jul. 22, 2011

(86) PCT No.: PCT/EP2011/003682
§ 371 (c)(1),
(2), (4) Date: Feb. 21, 2013

(87) PCT Pub. No.: WO2012/010320
PCT Pub. Date: Jan. 26, 2012

(65) Prior Publication Data
US 2013/0139901 A1 Jun. 6, 2013

(30) Foreign Application Priority Data
Jul. 23, 2010 (DE) .......................... 10 2010 032 182

(51) Int. Cl.
*A61M 1/36* (2006.01)
*B08B 9/032* (2006.01)

(52) U.S. Cl.
CPC ........... *B08B 9/032* (2013.01); *A61M 1/3643* (2013.01); *A61M 1/3646* (2014.02);
(Continued)

(58) Field of Classification Search
CPC .............. A61M 1/3643; A61M 1/3646; A61M 1/3649; A61M 1/3652; A61M 2205/123; B08B 9/032
(Continued)

(56) References Cited

U.S. PATENT DOCUMENTS 5,125,915 A * 6/1992 Berry et al. ................... 604/533
5,776,091 A * 7/1998 Brugger et al. ................ 604/6.1
(Continued)

FOREIGN PATENT DOCUMENTS

| CN | 1658916 A | 8/2005 |
|---|---|---|
| CN | 101443057 A | 5/2009 |

(Continued)

OTHER PUBLICATIONS

International Search Report from PCT/EP2011/003682 mailed on Dec. 15, 2011.

*Primary Examiner* — Tatyana Zalukaeva
*Assistant Examiner* — Benjamin Klein
(74) *Attorney, Agent, or Firm* — Fish & Richardson P.C.

(57) ABSTRACT

A rinsing line for discharging a rinsing fluid out of a medical technical functional device having been rinsed by means of the rinsing fluid is described, in which the rinsing line is, on the one side, connected, provided or intended for being connected with a section of the medical technical functional device and in which the rinsing line is, on the other side, connected with, provided or intended for being connected with a fluid supplying device for supplying a medical fluid into the medical technical functional device. A medical technical functional device, a medical technical treatment apparatus, a method and a control unit are also described.

11 Claims, 2 Drawing Sheets

(52) U.S. Cl.
CPC ........ *A61M 1/3649* (2014.02); *A61M 1/3652* (2014.02); *A61M 2205/123* (2013.01); *Y10T 137/0424* (2015.04); *Y10T 137/4245* (2015.04)

(58) Field of Classification Search
USPC ................................................ 604/4.01–6.16
See application file for complete search history.

(56) References Cited

U.S. PATENT DOCUMENTS

| | | |
|---|---|---|
| 2008/0146996 A1 | 6/2008 | Smisson et al. |
| 2009/0114593 A1* | 5/2009 | Fischer ............... A61M 1/3643 210/636 |
| 2010/0038322 A1 | 2/2010 | Hedmann et al. |
| 2010/0116740 A1 | 5/2010 | Fulkerson et al. |
| 2012/0080437 A1 | 4/2012 | Guenther et al. |
| 2012/0265117 A1* | 10/2012 | Fava et al. ................... 604/6.09 |

FOREIGN PATENT DOCUMENTS

| | | | |
|---|---|---|---|
| CN | 101511404 A | 8/2009 | |
| DE | 4220647 A1 | 1/1994 | |
| DE | 4240681 A1 | 6/1994 | |
| DE | 198 24 015 C1 | 8/1999 | |
| DE | 199 25 297 C1 | 7/2000 | |
| DE | 10 2006 022122 A1 | 11/2007 | |
| DE | 10 2009 012 632 A1 | 9/2010 | |
| DE | 10 2009 018 664 A1 | 10/2010 | |
| DE | 10 2009 024 468 A1 | 12/2010 | |
| DE | 10 2010 032 18 A1 | 1/2012 | |
| EP | 0 560 368 A2 | 9/1993 | |
| EP | 1 057 493 A2 | 12/2000 | |
| EP | 1 454 643 A1 | 9/2004 | |
| IT | WO 2008125893 A1 * | 10/2008 | .......... A61M 1/3643 |
| JP | H10155899 A | 6/1998 | |
| JP | 2009536537 A | 10/2009 | |
| WO | 99/20376 A1 | 4/1999 | |
| WO | 9920376 A1 | 4/1999 | |
| WO | 02/062454 A1 | 8/2002 | |
| WO | 2007131611 A2 | 11/2007 | |
| WO | 2008/028579 A1 | 3/2008 | |

\* cited by examiner

RINSING LINE, MEDICAL TECHNICAL FUNCTIONAL DEVICE, MEDICAL TECHNICAL TREATMENT APPARATUS AND METHOD

CROSS REFERENCE TO RELATED APPLICATIONS

The present application is the national stage entry of International Patent Application No. PCT/EP2011/003682, filed Jul. 22, 2011, which claims priority to Application No. DE 10 2010 032 182.6, filed in the Federal Republic of Germany on Jul. 23, 2010.

FIELD OF INVENTION

The present invention relates to a rinsing line. It further relates to a medical technical functional device, a medical technical treatment apparatus, a method and a control unit.

BACKGROUND INFORMATION

Rinsing or flushing medical technical functional devices, e.g., prior to and/or after their use in connection with a medical treatment, is known from practice.

SUMMARY

One object of the present invention is to propose a rinsing line suited for this purpose. Furthermore, an appropriate method for rinsing or flushing and/or priming a medical technical functional device is to be provided.

All advantages achievable by means of the rinsing line according to the present invention may undiminishedly also be obtained by means of the medical technical functional device, the medical technical treatment apparatus, the method and/or the control unit.

According to the present invention, a rinsing line suited and provided or intended for discharging a rinsing fluid out of a medical technical functional device having been rinsed by means of the rinsing fluid is proposed.

On the one hand or at one of its ends or fluid connection sections or portions, respectively, the rinsing line according to the present invention is connected or is in fluid connection with a section, segment or portion, respectively, of the medical technical functional device, or the rinsing line according to the present invention is intended or provided for being connected with the said section, segment or portion, respectively.

On the other hand or at one of its end or fluid connection sections or segments, respectively, the rinsing line according to the present invention is connected with—or provided or intended for being connected with—a fluid supplying device for supplying or introducing a medical fluid into the medical technical functional device.

The medical technical functional device according to the present invention (in the following also shortly referred to as: functional device) is provided or intended for being connected with or is connected with at least one rinsing line according to the present invention.

The medical technical treatment apparatus according to the present invention (in the following also shortly referred to as: treatment apparatus) is provided or intended for being connected with or is connected with at least one rinsing line according to the present invention and/or with a medical technical functional device according to the present invention.

The method according to the present invention serves for rinsing or flushing and/or priming a medical technical functional device or a functional device, respectively, and comprises the use of a rinsing line according to the present invention.

The control unit according to the invention is provided or intended and configured for automatically performing or executing at least one of the steps of a rinsing or flushing and/or priming method, in particular of a rinsing or flushing and/or priming method according to the present invention.

The control unit according to the present invention is particularly provided or intended for being used with a medical technical treatment apparatus.

Exemplary embodiments according to the present invention may comprise some or all of the following features in any arbitrary combination.

In certain exemplary embodiments of the present invention, the term "discharging" as used herein refers to dragging out and/or draining or diverting a rinsing or flushing fluid, respectively, out of the functional device, preferably via the fluid supplying device that is in this case not only designed or embodied and provided or intended for discharging but also for supplying, further preferably into a treatment apparatus.

In certain exemplary embodiments of the present invention, a "rinsing fluid" is to be understood as a fluid that is suited and provided or intended for rinsing or flushing and/or priming a functional device.

Non-limiting examples include substitute liquid, sterilization fluids, and the like, gases such as sterile air, as well as combinations or mixtures thereof.

In certain exemplary embodiments of the present invention, a connection of the rinsing line with a segment, section or portion, respectively, of the functional device states that the rinsing line is provided or intended for a fluid connection with a fluid-conducting interior of the said segment, section or portion, respectively, of the functional device or is in fluid connection with the latter. In such embodiments, a fluid exchange between an interior of the rinsing line and the interior of the section of the functional device is provided or intended.

In some exemplary embodiments according to the present invention, the section of the medical technical functional device or functional device, respectively, is a fluid (e.g., blood or rinsing liquid) conducting section—at least in certain methods in which a patient is treated according to intended use of the functional device.

In certain exemplary embodiments of the present invention, a connection of the rinsing line with a fluid supplying device states that the rinsing line is provided or intended for a fluid connection with a fluid-conducting interior of the fluid supplying device or is in fluid connection with the latter.

The term "fluid supplying device" as used herein refers to a device that is suited and/or provided or intended for supplying and/or discharging at least one medical fluid into the functional device or out of the functional device.

In certain exemplary embodiments of the present invention, a "medical fluid" refers to a treatment fluid that is or can be used during the patient's treatment. Non-limiting examples hereof generally include liquids such as blood, dialysate, substituate liquid, drug solutions, priming and/or rinsing or flushing and/or sterilization fluids, and the like, as well as combinations or mixtures thereof.

In certain exemplary embodiments of the present invention, the medical fluid and the rinsing fluid may be of the same kind and/or identical. However, this does not have to be the case.

In some exemplary embodiments according to the present invention, the rinsing fluid is identical to the fluid that was introduced as the medical fluid at an earlier point of time. In certain exemplary embodiments according to the present invention, the rinsing fluid is a substitute that is, e.g., used in certain dialyzing methods. In some exemplary embodiments according to the present invention, both the medical fluid and the rinsing fluid are supplied to the functional device via the fluid supplying device. In some exemplary embodiments according to the present invention, both the medical fluid and the rinsing fluid are discharged out of the functional device via the fluid supplying device.

In certain exemplary embodiments according to the present invention, both the medical fluid and the rinsing fluid are prepared online in the treatment apparatus used for treating the patient.

In certain exemplary embodiments of the present invention, the fluid supplying device is a connection section or part of a connection section provided or intended for establishing a fluid connection, preferably an immediate fluid connection, between the functional device and the medical technical treatment apparatus or the treatment apparatus, respectively.

In certain exemplary embodiments of the present invention, the connection section or the fluid supplying device is at least also provided or intended for supplying or introducing the medical fluid from the medical technical treatment apparatus into the medical technical functional device or for transferring, transmitting, and the like, the medical fluid from the medical technical treatment apparatus to the medical technical functional device.

In certain exemplary embodiments of the present invention, the fluid supplying device is a port for supplying substituate liquid into the functional device.

In some exemplary embodiments, supplying substituate liquid is carried out during an extracorporeal treatment in form of a pre- and/or post-dilution.

In certain exemplary embodiments of the present invention, the fluid supplying device is or comprises a biluminal or double-lumen connection section or junction portion, respectively.

Such a biluminal connection section is suited and/or provided or intended for concurrently conducting at least two fluids that are different from each other.

In certain exemplary embodiments, the biluminal connection section comprises a first lumen provided or intended for receiving and/or conducting the medical fluid. It further comprises a second lumen provided or intended for receiving and/or conducting the rinsing fluid or flushing fluid, respectively.

In those exemplary embodiments, in particular the first lumen of the biluminal connection section is in fluid connection with a fluid line of the functional device for the medical fluid; the second lumen of the biluminal connection section is in fluid connection with the rinsing line for the rinsing fluid, or vice versa.

In certain exemplary embodiments of the present invention, the term "concurrently conducting" at least two fluids refers to contemporaneously or simultaneously, respectively, i.e., taking place at the same point of time, within the same time interval, and the like, receiving and/or conducting or directing the fluids, e.g., the medical fluid and the rinsing fluid.

Thereby, the rinsing fluid and the medical fluid may flow in counterflow. However, they can also flow in directions not being opposite to each other.

In certain exemplary embodiments of the present invention, the functional device is or comprises an extracorporeal blood circuit.

In some exemplary embodiments of the present invention, the functional device is or comprises a blood cassette.

In certain exemplary embodiments of the present invention, the section of the functional device designed or embodied as an extracorporeal blood circuit is a section, segment or portion, respectively, of an arterial line section of the extracorporeal blood circuit.

In certain exemplary embodiments of the present invention, the section of the functional device embodied or designed as an extracorporeal blood circuit is arranged between a blood pump or an intervention or engagement section of the extracorporeal blood circuit for a blood pump and an extracorporeal blood treatment device such as, e.g., a blood filter or a dialyzer.

A "blood pump" as used herein, for example, refers to a displacement pump, such as a tube pump or a peristaltic pump, or any other pump that is provided or intended and/or designed or embodied for conveying blood (e.g., by displacing) out of a first section of the extracorporeal blood circuit into a second section of the extracorporeal blood circuit during an extracorporeal blood treatment procedure.

In certain exemplary embodiments of the present invention, the term "intervention or engaging section for a blood pump" as used herein refers to a section of the extracorporeal blood circuit at which the blood pump interacts with the said section according to its intended use for displacing or conveying the blood or at which the blood pump is connected with the extracorporeal blood circuit for this purpose.

However, without being limited thereto, examples of an extracorporeal blood treatment device comprise a blood filter for cleaning patient blood in connection with a hemodialysis, hemofiltration and/or hemodiafiltration treatment, and the like. The extracorporeal blood treatment device may be designed or embodied as a one-way product or a disposable device or article, respectively.

In certain exemplary embodiments of the present invention, the section of the extracorporeal blood circuit is arranged between the blood pump or the intervention or engaging section of the extracorporeal blood circuit for the blood pump of the extracorporeal blood circuit and a pre-dilution access of the extracorporeal blood circuit.

In some exemplary embodiments of the present invention, the rinsing line according to the present invention is an additional element of the functional device. Here, "additional" means that the functional device may also be used if the rinsing line according to the present invention is not used. In particular, all methods and functions described in embodiments of German Application No. DE 10 2009 018 664.6 of the applicant of the present invention having the title "Externe Funktionseinrichtung, Blutbehandlungsvorrichtung zum Aufnehmen einer erfindungsgemäßen externen Funktionseinrichtung, sowie Verfahren" and having been filed with the German Patent and Trademark Office on Apr. 23, 2009, as well as of German Application No. DE 10 2009 024 468.9 of the applicant of the present invention having the same title and having been filed with the German Patent and Trademark Office on Jun. 10, 2009, can be carried out with a correspondingly designed functional device not using the rinsing line according to the present invention. Only the special functions that shall be enabled by means of the rinsing line according to the present invention could not be performed by means of a functional device not comprising such a rinsing line according to the present invention. In such exemplary embodiments, the rinsing line can be connected with the functional device and the fluid supplying device after manufacture. Without being limited thereto, it may be attached in a manner such as to be mounted and/or snapped on, screwed on and/or with, clipped on or in any other way releasably or unreleasably fixed such as welded, adhered, and the like. Alternatively, it may, however, also be connected or manufactured with the rinsing line according to the present invention industrially or outside the factory, integrally or in one piece. Also in this case, the rinsing line according to the present invention may be referred to as an additional element of the functional device.

In certain exemplary embodiments of the present invention, the rinsing line is integrated into or integrally manufactured with, respectively, the functional device in form of a flow channel. In those exemplary embodiments, as described above, the rinsing line may be connected with the fluid supplying device after its manufacture.

In certain exemplary embodiments of the present invention, the rinsing line is connected with or intended or provided for being connected with the section of the functional device by means of an automatic or electively actuable rinsing valve.

In some exemplary embodiments according to the present invention, the rinsing valve is a part or constituent, respectively, of the rinsing line; in other exemplary embodiments, it is a part or constituent of the functional device.

In certain exemplary embodiments according to the present invention, the rinsing line can be closed and/or opened by means of the rinsing valve.

In some exemplary embodiments according to the present invention, the rinsing valve is designed or embodied as a phantom valve.

The term "phantom valve" as used herein refers to an element comprising an actuator surface or plane, respectively, reachable by means of an actuator (here, for example, an actuator membrane) that may fulfill the function of a valve.

The actuator membrane can be moved, expanded or bent, respectively, or the like, in one direction by applying a force thereon, e.g., a pressure force. By moving or expanding the actuator membrane, the latter may be attached to or moved away from an element such as a sealing element, for example, a bar. Thus, the actuator membrane can, for example, effect or enhance, respectively, or terminate or reduce, respectively, a sealing effect.

When the force is released from the actuator membrane again, the latter can return into a basic position, e.g., an unbent state or position.

A phantom valve can be or will be designed or embodied with or from a bar section of a channel at or of a hard or solid part of the blood cassette and a section of a film thereof contacting or facing the bar section.

Phantom valves may be actuated by means of actuators of the blood treatment apparatus.

For closing a phantom valve, the section of a film (that is, in certain exemplary embodiments, used for covering the hard or solid part of the blood cassette) may be pressed onto the bar section. For opening the phantom valve, the film section may be re-lifted from the bar section.

Further examples and/or exemplary embodiments of phantom valves can be derived from German Application No. DE 10 2009 012 632.5 having the title "Abdichtungseinrichtung zum Abdichten eines Volumens einer medizinischen Behandlungsanordnung gegen ein weiteres Volumen sowie Anordnung and Verfahren" ("A sealing means for sealing a volume of a medical treatment arrangement against another volume, as well as an arrangement and a method") that has been filed with the German Patent and Trademark Office on Mar. 10, 2009 by the present applicant. The respective disclosure thereof is fully incorporated herein in its entirety by reference thereto.

In certain exemplary embodiments, the functional device comprises at least one coupling device as a port or a fluid supplying device comprising an inner tubing segment having a first lumen and an outer tubing segment having a second lumen, wherein the outer tubing segment is arranged at least around one portion, section, segment or area, respectively, of the inner tubing segment such that a space is formed within the second lumen between the exterior of the inner tubing segment and the outer tubing segment, wherein the first lumen of the inner tubing segment is provided or intended for receiving and/or conducting the medical fluid and the space of the outer tubing segment is provided or intended for receiving and/or conducting at least the rinsing fluid, or vice versa.

Appropriate examples of such a port include those exemplary embodiments disclosed in German Application No. DE 10 2010 032 181.8 to the present applicant having the title "Ankoppeleinrichtung, Konnektor, medizintechnische Funktionseinrichtung, medizintechnische Behandlungsvorrichtung sowie Verfahren" ("Coupling device, connector, medico-technical functional device, medico-technical treatment device and method") that has been filed with the German Patent and Trademark Office on Jul. 23, 2010. The respective content of said application is fully incorporated herein in its entirety by reference thereto.

In certain exemplary embodiments of the present invention, the functional device is embodied or designed as an extracorporeal blood tubing set or comprises such an extracorporeal blood tubing set.

In certain exemplary embodiments of the present invention, the functional device is embodied or designed as a blood cassette, as a part of such a blood cassette or comprises such a blood cassette. Such a blood cassette can, for example, be designed or embodied as a cast part or an injection molded part. Independently thereof, it may be designed or embodied as a one-way blood cassette or a disposable blood cassette.

Without being limited thereto, examples of appropriate blood cassettes include those embodiments described in German Application No. DE 10 2009 018 664.6 of the applicant of the present application having the title "Externe Funktionseinrichtung, Blutbehandlungsvorrichtung zum Aufnehmen einer erfindungsgemäßen externen Funktionseinrichtung, sowie Verfahren" ("External functional means, blood treatment apparatus for receiving an external functional means in accordance with the invention, and method") that has been filed with the German Patent and Trademark Office on Apr. 23, 2009, as well as those embodiments described in German Application No. DE 10 2009 024 468.9 of the applicant of the present application having the title "Externe Funktionseinrichtung, Blutbehandlungsvorrichtung zum Aufnehmen einer erfindungsgemäßen externen Funktionseinrichtung, sowie Verfahren" ("External functional means, blood treatment apparatus for receiving an external functional means in accordance with the invention, and method") that has been filed with the German Patent and Trademark Office on Jun. 10, 2009. The embodiments disclosed in said applications are fully incorporated herein in their entirety by reference thereto.

In certain exemplary embodiments, the treatment apparatus according to the present invention is designed or embodied as an extracorporeal treatment apparatus, in particular as an extracorporeal blood treatment apparatus, such as a dialyzing apparatus—for example, for use in connection with a single-needle or double-needle dialysis treatment—in particular as a hemodialysis apparatus, a hemofiltration apparatus, a hemodiafiltration apparatus, or as an apparatus for adsorption, liver support therapy, apheresis, transfusion, etc.

In certain exemplary embodiments of the method according to the present invention, it is intended to completely or at least partially discharge or drain, respectively, rinsing fluid present in the medical technical functional device having been rinsed through the rinsing line into a port or a machine connector for introducing substitute liquid from the medical technical treatment apparatus into the medical technical functional device.

In certain exemplary embodiments of the method according to the present invention, in a first step, substitute liquid is introduced into the functional device.

The substitute liquid is conveyed within an interior of the functional device in order to rinse or flush and/or prime the functional device.

In certain exemplary embodiments of the method according to the present invention, rinsing or flushing and/or priming is carried out with a certain or predetermined rinsing level or amount of substitute liquid.

In some exemplary embodiments according to the present invention, the rinsing line is closed after terminating the rinsing procedure. A corresponding device can be provided at one or both ends of the rinsing line.

All, a few or some steps of a method according to the present invention such as will be exemplarily and in a non-limiting way described with reference to the appended drawings may be performed automatically.

Furthermore, the object according to the present invention is also solved by a digital storage device, a computer program product and a computer program.

A digital storage device, in particular a disk, a RAM, ROM, a CD or DVD, comprising electrically readable control signals can interact with a programmable computer system such that the execution of the technical steps of a method according to the present invention is prompted.

Thereby, the execution of all, a few or some of the technically performed steps of the method according to the present invention can be prompted.

A computer program product comprises a program code stored on a machine readable medium for prompting the execution of the technical steps of the method according to the present invention when executing the computer program product on a computer.

In certain exemplary embodiments of the present invention, the term "machine readable medium" as used herein refers to a medium containing data or information that are interpretable by software and/or hardware. The medium may be a data medium such as a disk, a RAM, ROM, a CD, DVD, a USB flash drive, a flashcard, a SD card, and the like.

A computer program comprises a program code for prompting the execution of the technical steps of a method according to the present invention when executing the computer program on a computer.

The execution of all, a few or some of the technical steps of the method according to the present invention may be prompted with the computer program product and the computer program as well.

Certain exemplary embodiments according to the present invention comprise one or more of the following advantages.

The present invention provides a rinsing line that may, in some exemplary embodiments according to the present invention, contribute to reducing the constructional effort when manufacturing an arrangement for treating a patient in an advantageously simple manner. In turn, this advantageously contributes to reducing the cost effort.

As the rinsing line according to the present invention is a separate component of the functional device, an extracorporeal blood circuit may, in certain exemplary embodiments of the present invention, be delivered with pre-connected line sections (arterial and venous patient lines) such that covering caps otherwise required for protecting the patient lines may advantageously be omitted. The latter may contribute to cost reduction and to reducing a contamination risk.

As the rinsing line according to the present invention is easily connectable with a port of the functional device, a rinse port on the machine side as well as at least one hydraulic valve may advantageously be omitted in certain exemplary embodiments of the present invention. Without requiring any additional effort, this may advantageously be achieved with a pre-existing port for supplying substitute liquid, in particular with a port as disclosed in German Application No. DE 10 2010 032 181.1 of the present applicant having the title "Ankoppeleinrichtung, Konnektor, medizintechnische Funktionseinrichtung, medizintechnische Behandlungsvorrichtung sowie Verfahren" ("Coupling device, connector, medico-technical functional device, medico-technical treatment device and method") that has been filed with the German Patent and Trademark Office on Jul. 23, 2010.

As it is in certain exemplary embodiments of the present invention advantageously possible to use a simple adaptor for connection with the rinse port of the machine, it may advantageously be possible to omit disposable components such as, for example, a rinse port adaptor comprising at least three covering caps such as known from state of the art.

In this way, it may advantageously be possible to reduce costs for the manufacture and/or use of the functional device according to the present invention, in particular in form of a disposable blood cassette.

In certain exemplary embodiments, the present invention advantageously provides usability and/or hygiene advantages because manual fluidic connections may advantageously be omitted. This may in turn contribute to saving working time and effort and to improving the ergonomics. Furthermore, it may contribute to enhancing safety against contaminations.

In the following, exemplary embodiments of the present invention will be described with reference to the appended drawings. In the drawings, identical reference numerals refer to same or identical elements.

DETAILED DESCRIPTION

Figure 1:
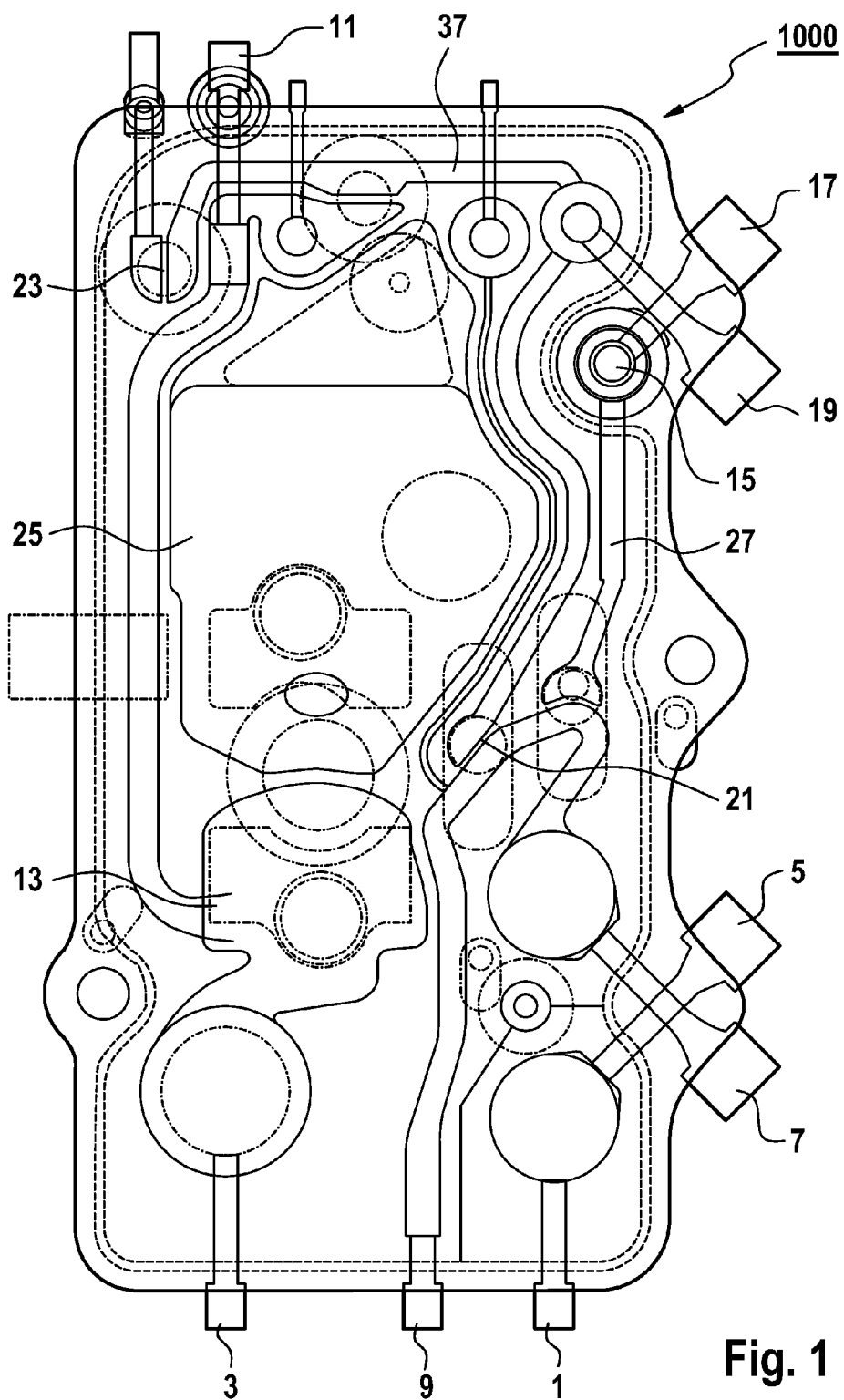
FIG. 1 shows a front view of a medical technical functional device of the present invention.

FIG. 1 shows a front view of a medical technical functional device 1000 according to the present invention.

The functional device 1000 is designed or embodied as a blood cassette (in the following shortly referred to as: cassette).

The cassette 1000 comprises an arterial patient access 1 as well as a venous patient access 3.

The cassette 1000 comprises a connector 5 for discharging blood out of the blood cassette 1000 as well as a connector 7 for introducing blood into the cassette 1000.

Both connectors 5 and 7 are connectable or connected with a pump tubing segment or set of a blood pump (not shown in FIG. 1).

The cassette 1000 comprises an arterial filter line 9 as well as a venous filter line 11.

The cassette's 1000 interior comprises a venous blood chamber 13.

The cassette 1000 comprises an addition site 15 for adding substituate liquid into the cassette 1000. The substituate liquid can be a substituate liquid having been prepared online by the treatment apparatus.

For further details of elements, components or constituents of the cassette shown in FIG. 1, it is referred to the afore-mentioned German Application Nos. DE 10 2009 018 664.6 and DE 10 2009 024 468.9 of the applicant of the present application, in particular to FIGS. 17 to 24 therein.

The addition site 15 for substituate liquid comprises a substituate port (not shown in FIG. 1).

The substituate port can be a port as described in German Application No. DE 10 2010 032 181.1 of the present applicant having the title "Ankoppeleinrichtung, Konnektor, medizintechnische Funktionseinrichtung, medizintechnische Behandlungsvorrichtung sowie Verfahren" ("Coupling device, connector, medico-technical functional device, medico-technical treatment device and method") that has been filed with the German Patent and Trademark Office on Jul. 23, 2010. The respective disclosure thereof is fully incorporated herein in its entirety by reference thereto.

The cassette 1000 comprises a connector 17 for discharging substituate out of the cassette 1000 as well as a connector 19 for introducing substituate into the cassette 1000, wherein the connectors 17 and 19 are connectable with a pump tubing segment or set of a substituate pump (not shown in FIG. 1) for the purpose of conveying the substituate liquid within an interior of the cassette 1000.

The cassette 1000 comprises a substituate line 37, a predilution access 21 and a postdilution access 23.

The cassette 1000 that is—exemplarily and without being limited to this exemplary embodiment—designed as a single-needle blood treatment cassette comprises a single-needle chamber 25.

The cassette 1000 comprises a rinsing line 27 according to the present invention.

In the example of FIG. 1, the rinsing line 27 is arranged between the addition site 15 for substituate liquid, i.e., a fluid supplying device, and the predilution access 21.

In the following, the execution or performance of the method according to the present invention will be described with reference to FIG. 2 in an exemplary embodiment using a single-needle treatment cassette.

Substituate liquid is exemplarily used as a rinsing or flushing and/or priming liquid; however, the present invention is again not limited to this example.

Figure 2:
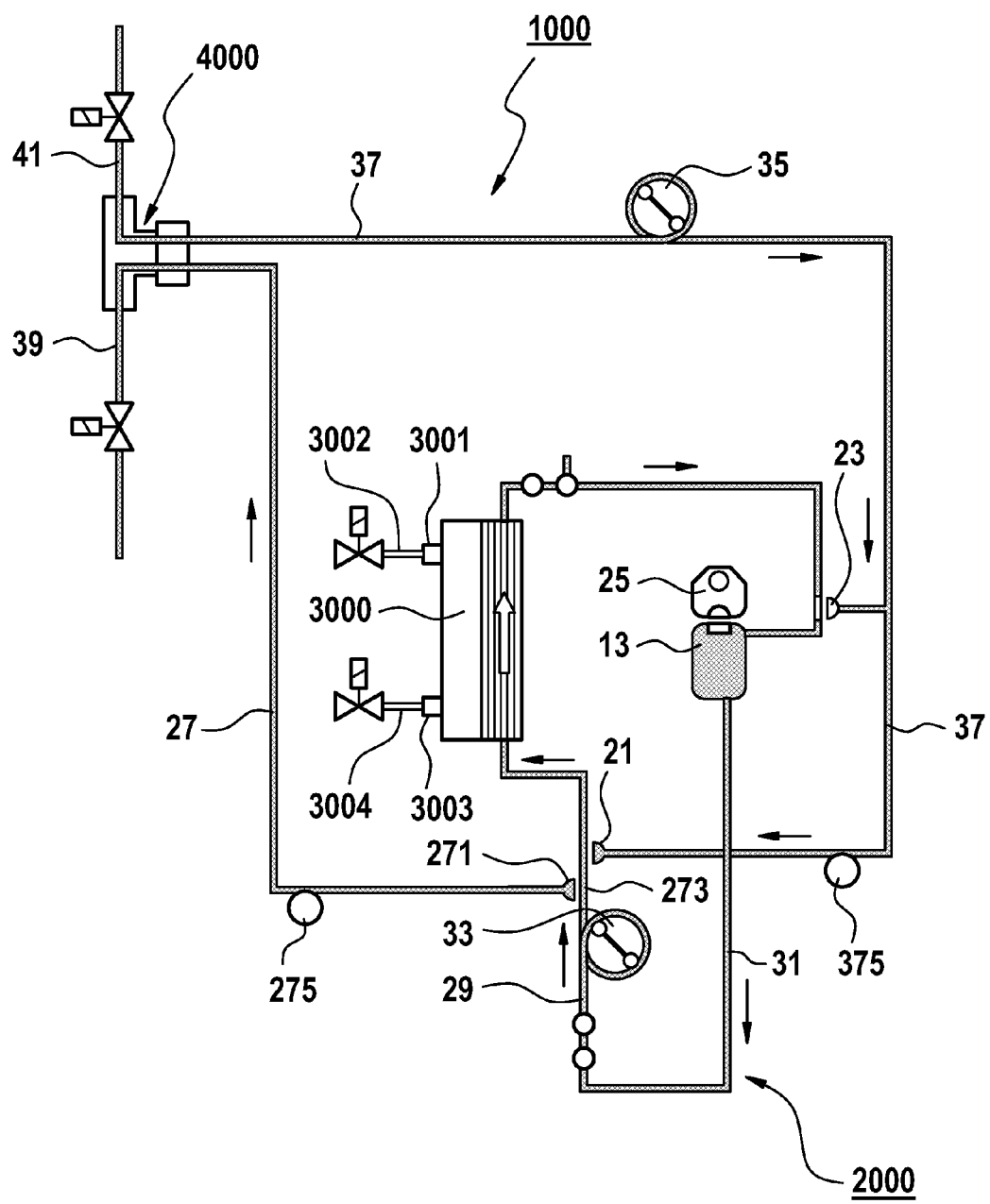
FIG. 2 shows, in a schematically simplified manner, a medical technical functional device for performing a rinsing or flushing and/or priming method according to the present invention.

In a schematically simplified manner, FIG. 2 shows a functional device 1000 according to the present invention for performing a rinsing or flushing and/or priming method according to the present invention.

The functional device 1000 comprises an extracorporeal blood circuit 2000. The extracorporeal blood circuit 2000 comprises an arterial line section 29 as well as a venous line section 31.

The arterial line section 29 and the venous line section 31 are short-circuited. Herefor, a standard straight connector may be used.

A blood pump 33 is arranged in the arterial line section 29.

A substituate pump 35 is arranged in the substituate line 37.

A treatment device 3000 between the arterial line section 29 and the venous line section 31 serves for extracorporeally treating blood.

Exemplarily being designed as a dialysis device (also referred to as a blood filter), the treatment device 3000 comprises a dialysate inlet 3001 at a respective dialysate supply line 3002 as well as a dialysate outlet 3003 at a respective dialysate drain line 3004.

The rinsing line 27 comprises a rinsing valve 271. The rinsing valve 271 may, however, also be part of the functional device 1000; furthermore, the rinsing valve 271 may also be part of the rinsing line 27 and the functional device 1000.

The rinsing line 27 branches off from the functional device 1000 or a fluid-conducting section thereof, respectively, in the range of a rinsing branch or a rinsing junction 273, respectively.

The rinsing line 27 further comprises an optional first blood detection sensor 275 (e.g., an optical sensor).

The rinsing line 27 ends in a substituate port 4000. In the substituate port 4000, the rinsing line 27 branches off to a drain line 39.

The substituate line 37 extends or leads from the substituate port 4000 to the extracorporeal blood circuit 2000. The substituate line 37 is supplied with fresh substituate from a substituate liquid source (not shown) via a supply line 41.

In the substituate line 37, a second blood detection sensor 375 (e.g., an optical sensor) is arranged.

For performing the rinsing or flushing and/or priming method according to the present invention, the venous chamber 13 is filled at first.

Herefor, the substituate pump 35 conveys substituate liquid, for example, with a defined flow—the latter may be set by the user—via the postdilution access 23 into the venous chamber 13. A venous clamp (not shown in FIG. 2) may thereby be closed.

The substituate liquid flows from the venous chamber 13 through an opened single-needle valve (not shown in FIG. 2) that is connected with the single-needle chamber 25 into the single-needle chamber 25. The single-needle chamber 25 is preferably opened to the surroundings. In certain exemplary embodiments, ventilation may be effected via a connection that can be opened at or on the single-needle chamber 25—e.g., a ventilation valve arranged at or on the single-needle chamber 25.

As soon as a level has been detected in the venous chamber 13, arterial and venous tubing clamps (not shown in FIG. 2, respectively) are opened in order to fill the arterial and the venous line sections.

The blood pump 33 is started with a defined flow, and the substituate pump 35 is stopped.

As soon as the level in the venous chamber 13 has dropped appropriately, the substituate pump 35 is started with a volume flow larger than the volume flow of the blood pump 33. Hereby, the blood pump 33 is still running.

Thereby, the venous chamber 13 is filled again. The substitute pump 35 will be stopped, when the level in the venous chamber 13 has been detected and, additionally, a defined volume has been conveyed by means of the substituate pump 35 thereafter.

If liquid is detected at the arterial air detector (not shown in FIG. 2), the blood pump 33 conveys a defined volume for filling the blood pump tubing and further on until the venous level has dropped.

For filling the treatment device 3000, the venous clamp and the postdilution valve of the postdilution access 23 are closed.

The substituate pump 35 conveys substituate liquid via the opened predilution valve of the predilution access 21 into the extracorporeal blood circuit until a level has been detected in the venous chamber 13. In this way, the treatment device 3000 is filled.

Subsequently, rinsing or flushing is started, wherein the extracorporeal blood circuit 2000 is completely filled with liquid. In certain exemplary embodiments of the present invention, rinsing or flushing, respectively, the extracorporeal circuit 2000 can be carried out immediately after filling.

In certain exemplary embodiments, rinsing or flushing serves for removing particles from the extracorporeal blood circuit 2000 and the treatment device 3000 in order to avoid any incorporation thereof into the patient.

As the arterial line section 29 and the venous line section 31 are short-circuited, rinsing or flushing in a single-pass procedure is not possible. In those exemplary embodiments, the method according to the present invention may advantageously consider and correspondingly avoid a possible recirculation as described below.

The treatment device 3000 is filled with substituate liquid on the blood side. The extracorporeal blood circuit 2000 is free from air.

For filling the single-needle chamber 25, the substituate pump 35 conveys with a defined flow via the predilution valve of the predilution access 21.

Thereby, substituate liquid is introduced via the treatment device 3000 into the single-needle chamber 25. The single-needle valve as well as a ventilation valve at or on the single-needle chamber 25 are opened.

Arterial and venous clamps (not shown in FIG. 2) are closed. The rinsing valve 271 is closed. The blood pump 33 is not operated.

As soon as a level has been detected in the single-needle chamber 25, the latter is filled volumetrically.

When the volumetric filling of the single-needle chamber 25 has been finished, the ventilation valve at or on the single-needle chamber 25 is closed.

The rinsing valve 271 is being opened.

Additionally, the arterial and the venous clamp are opened, preferably at the same time.

The blood pump 33 is started with a flow significantly lower than the flow of the substituate pump 35. Thus, the substituate flow is divided at the predilution access 21. One portion of the substituate liquid is directly discarded into the rinsing line 27, the other portion—that is initially only defined by the conveyance rate of the blood pump 33—flows through the treatment device 3000.

The flow path of the substituate liquid is illustrated in FIG. 2 by means of a block arrow.

If the flow of the substituate pump 35 is sufficiently high, the complete substituate fluid conveyed by means of the blood pump 33 flows into the rinsing line 27. In certain exemplary embodiments of the method according to the present invention, a repulsion can be ruled out at a relation of blood pump rate to substituate pump rate of 1:2.

In this way, it may advantageously be possible to inhibit an overpulsing or overflowing, respectively, of the substituate liquid through the predilution access 21 back into the substituate line 37. A recirculation of the substituate liquid may thus advantageously be avoided.

In order to reduce the level in the single-needle chamber 25, air is conveyed into the single-needle chamber 25 by means of a single-needle compressor (not shown in FIG. 2).

Air can be conveyed as long as a venous level detector (not shown in FIG. 2) does not detect a level anymore.

In order to avoid that "used" liquid, i.e., liquid having been used for rinsing or flushing, respectively, and/or priming the functional device 1000, is pushed back or opposite, respectively, to the usual flow direction through the treatment device 3000, the volume flow resulting from emptying the single-needle chamber 25 will, in certain exemplary embodiments, be set such that it does not exceed the flow of the blood pump 33.

The venous level detector and the pressure within the single-needle container are used for reducing the liquid level within the venous chamber 13 as much as possible.

If a predetermined level has been reached, the blood pump 33 is stopped.

The venous clamp and the ventilation valve at or on the single-needle chamber 25 are closed. The single-needle compressor is stopped.

For determining the amount of rinsing liquid, the flow conveyed by means of the blood pump 33 can be considered. If a defined value has been reached, the rinsing process will be finished.

If this is not the case, in certain exemplary embodiments, the single needle chamber 25 can be filled again and rinsing can be continued.

The invention claimed is:

1. A medical technical functional device comprising:
   a rinsing line configured to discharge a rinsing fluid out of the medical technical functional device which was rinsed or flushed with the rinsing fluid;
   an extracorporeal blood circuit comprising an arterial line section, wherein a blood pump is arranged along the arterial line section;
   a predilution access, wherein a portion of the arterial line section extends from the blood pump to the predilution access; and
   a rinsing valve directly connected to the rinsing line and directly connected to the portion of the arterial line section that extends from the blood pump to the predilution access,
   wherein the rinsing line is connected with or configured to be connected with a fluid supplying device configured to supply a medical fluid into the medical technical functional device.

2. The medical technical functional device according to claim 1, further comprising:
   a port, the port comprising at least:
      an inner tubing segment having a first lumen; and
      an outer tubing segment having a second lumen, wherein the outer tubing segment is arranged at least around one area of the inner tubing segment such that a space is formed within the second lumen between an exterior of the inner tubing segment and the outer tubing segment;
      wherein the first lumen of the inner tubing segment is configured to at least one of receive or conduct the medical fluid, and wherein the space of the outer tubing segment is configured to at least one of receive or conduct at least the rinsing fluid, or vice versa.

3. The medical technical functional device according to claim 1, wherein the medical technical functional device is configured as one of an extracorporeal blood tubing set, a blood treatment cassette, or a disposable blood treatment cassette.

4. A medical technical treatment apparatus, connected with or configured to be connected with at least one medical technical functional device according to claim 1.

5. A method comprising at least one of rinsing, flushing or priming the medical technical functional device according to claim 1.

6. The method according to claim 5, further comprising:
at least partially discharging or draining, respectively, the rinsing fluid out of the rinsed medical technical functional device through the rinsing line into a port or a machine connector for supplying substituate liquid from a medical technical treatment apparatus into the medical technical functional device.

7. A control unit, configured to be used with the medical technical treatment apparatus according to claim 4, and configured for automatically performing or executing the method of at least one of rinsing, flushing or priming the at least one medical technical functional device.

8. The medical technical functional device according to claim 1, wherein the medical technical functional device further comprises the fluid supplying device, wherein the fluid supplying device is a port for supplying a substituate liquid into the medical technical functional device.

9. The medical technical functional device according to claim 1, wherein the medical technical functional device further comprises the fluid supplying device, wherein the fluid supplying device is or comprises a biluminal connection section configured to concurrently conduct two fluids.

10. The medical technical functional device according to claim 1, wherein the medical technical functional device further comprises a blood cassette.

11. The medical technical functional device according to claim 10, wherein the arterial line section of the extracorporeal blood circuit is arranged between (a) the blood pump or an intervention or engaging section of the extracorporeal blood circuit for the blood pump and (b) an extracorporeal blood treatment device.

* * * * *